(12) United States Patent
Nampoothiri K. et al.

(10) Patent No.: US 6,562,607 B2
(45) Date of Patent: May 13, 2003

(54) NUCLEOTIDE SEQUENCES CODING FOR THE CLS GENE

(75) Inventors: Madhavan Nampoothiri K., Kerala (IN); Bettina Möckel, Düsseldorf (DE); Walter Pfefferle, Halle (DE); Lothar Eggeling, Jülich (DE); Hermann Sahm, Jülich (DE)

(73) Assignees: Degussa-Huls Aktiengesellschaft, Frankfurt (DE); Forschungszentrum Julich GmbH, Julich (DE)

( * ) Notice: Subject to any disclaimer, the term of this patent is extended or adjusted under 35 U.S.C. 154(b) by 0 days.

(21) Appl. No.: 09/848,726

(22) Filed: May 4, 2001

(65) Prior Publication Data

US 2002/0102667 A1 Aug. 1, 2002

Related U.S. Application Data

(63) Continuation-in-part of application No. 09/577,844, filed on May 25, 2000, now abandoned.

(51) Int. Cl.[7] .............................. C12N 9/00; C12N 1/20; C12N 15/00; C07H 21/04
(52) U.S. Cl. ..................... 435/183; 536/23.2; 536/24.3; 536/24.32; 435/252.32; 435/320.1
(58) Field of Search .................... 435/252.32, 320.1, 435/183; 536/23.2, 24.32, 24.3

(56) References Cited

FOREIGN PATENT DOCUMENTS

| EP | 0 771 879 A1 | 5/1997 |
|---|---|---|
| EP | 1 108 790 A2 | 6/2001 |
| WO | WO 01/00805 A2 | 1/2001 |

OTHER PUBLICATIONS

Ohta A. et al. Molecular cloning of the csl gene responsible for cardiolipin synthesis in *E. coli* and phenotipic consequences of its amplification, J. Bacteriol. (1985), 163, 506–514.*
Nishijima S. et al. Disruption of *Escherichia coli* cls gene responsible for cardiolipin synthesis, J. Bacteriol. (1988), 170, 774–780.*
Hiraoka S. et al. Amplification and substantial purification of cardiolipin synthase of *E. coli*. J. Biochem. (1991), 110, 443–449.*
Ragolia L. et al. The effects of phosphoglycerides on *Escherichia coli* cardiolipin synthase, Biochim. Biophys. Acta, (1994), 1214, 323–332.*
Tropp B. E. Cardiolipin synthase from *Escherichia coli*, Biochim. Biophys. Acta (1997), 1348, 192–200.*
L. Eggeling, et al., "L–Glutamate and L–lysine: Traditional Products with Impetuous Developments," Applied Microbiology and Biotechnology, Aug. 8, 1999, vol. 52, pp. 146–153.
International Search Report for counterpart application No. PCT/EP''''''''''''''''''''''''''''01/04705, dated Nov. 22, 2001.

* cited by examiner

Primary Examiner—Ponnathapu Achutamurthy
Assistant Examiner—Malgorzata A. Walicka
(74) Attorney, Agent, or Firm—Smith, Gambrell & Russell

(57) ABSTRACT

This invention relates to a genetically modified coryneform bacterium, the cls gene of which is amplified, and to an isolated polynucleotide, which codes for cardiolipin synthase from coryneform bacteria and to a process for the fermentative production of L-amino acids with amplification of the cls gene in the bacteria and to the use of the polynucleotide as a primer or hybridization probe.

29 Claims, 1 Drawing Sheet

Figure 1: Plasmid map of pJC1cls
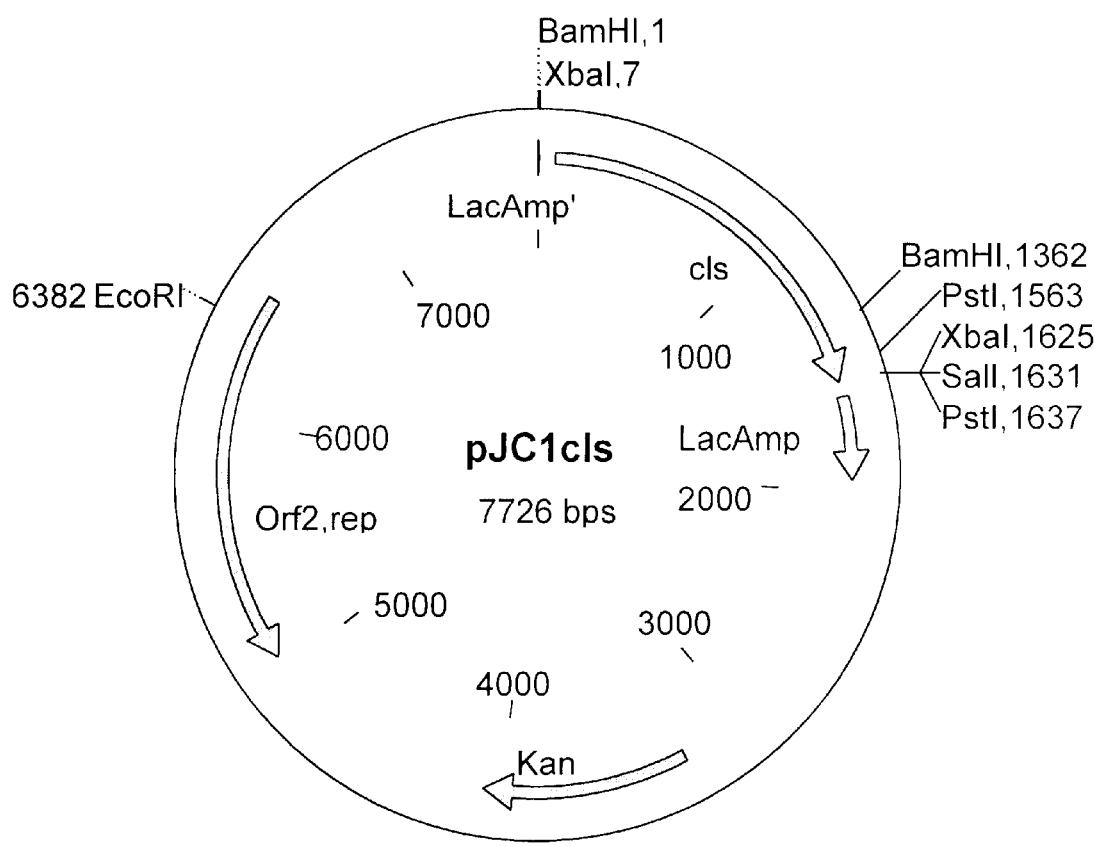

NUCLEOTIDE SEQUENCES CODING FOR THE CLS GENE

CROSS-REFERENCE TO RELATED APPLICATIONS

This application is a continuation-in-part of U.S. patent application Ser. No. 09/577,844 filed May 25, 2000, now abandoned, which is hereby incorporated by reference in its entirety.

The invention provides genetically modified coryneform bacteria, nucleotide sequences coding for cardiolipin synthase and a process for the fermentative production of amino acids, in particular L-glutamate, using coryneform bacteria, in which the cls gene, which codes for cardiolipin synthase, is amplified. All references cited herein are expressly incorporated by reference. Incorporation by reference is also designated by the term "I.B.R." following any citation.

PRIOR ART

Amino acids, in particular L-glutamate, are used in human medicine, in animal nutrition and in the pharmaceuticals industry, but in particular in the foodstuffs industry.

It is known that amino acids are produced by fermentation of strains of coryneform bacteria, in particular *Corynebacterium glutamicum*. Due to their great significance, efforts are constantly being made to improve the production process. Improvements to the process may relate to measures concerning fermentation technology, for example stirring and oxygen supply, or to the composition of the nutrient media, such as for example sugar concentration during fermentation, or to working up to yield the product by, for example, ion exchange chromatography, or to the intrinsic performance characteristics of the microorganism itself.

The performance characteristics of these microorganisms are improved using methods of mutagenesis, selection and mutant selection.

For some years, methods of recombinant DNA technology have moreover been used to improve strains of Corynebacterium which produce amino acids by amplifying individual amino acid biosynthesis genes and investigating the effect on amino acid production. Review articles on this subject may be found inter alia in Kinoshita ("Glutamic Acid Bacteria", in: Biology of Industrial Microorganisms, Demain and Solomon (Eds.) I.B.R., Benjamin Cummings, London, UK, 1985, 115–142) I.B.R., Hilliger (BioTec 2, 40–44 (1991)) I.B.R., Eggeling (Amino Acids 6:261–272 (1994)) I.B.R., Jetten and Sinskey (Critical Reviews in Biotechnology 15, 73–103 (1995)) I.B.R. and Sahm et al. (Annuals of the New York Academy of Science 782, 25–39 (1996)) I.B.R.

OBJECT OF THE INVENTION

The object of the present invention was to provide novel auxiliaries for the improved fermentative production of amino acids, in particular L-glutamate.

Amino acids, in particular L-glutamate, are used in human medicine, in animal nutrition, in the pharmaceuticals industry, and in particular in the foodstuffs industry. There is accordingly general interest in providing novel improved processes for the production of amino acids, in particular L-glutamate.

Any subsequent mention of L-glutamate or glutamate should be taken to mean not only the base, but also the salts thereof.

SUMMARY OF THE INVENTION

The new DNA sequence of *C. glutamicum* which codes for the cls gene and which as a constituent of the present invention is SEQ ID NO 1 and related sequences. The amino acid sequence of the corresponding gene product of the cls gene has furthermore been derived from the present DNA sequence. The resulting amino acid sequence of the cls gene product is SEQ ID NO 2 and related sequences.

BRIEF DESCRIPTION OF THE DRAWINGS

The present invention will be further understood with reference to the drawing offered here for illustration only and not in limitation of this invention.

FIG. 1 is a map of plasmidpJC1cls

DETAILED DESCRIPTION OF THE INVENTION

The invention provides a genetically modified coryneform bacterium, in which the cls gene, which codes for cardiolipin synthase, is amplified.

In this connection, the term "amplification" describes the increase in the intracellular activity of one or more enzymes in a microorganism, which enzymes are coded by the corresponding DNA.

Amplification may be achieved by means of various manipulations of the bacterial cell.

Amplification, in particular overexpression, may be achieved by increasing the copy number of the corresponding genes, by using a strong promoter or by mutating the promoter and regulation region or the ribosome-binding site located upstream from the structural gene. Expression cassettes incorporated upstream from the structural gene act in the same manner. It is additionally possible to increase expression during fermentative L-glutamate production by means of inducible promoters. It is also possible to use a gene which codes for a corresponding enzyme having an elevated activity. Expression is also improved by measures to extend the lifetime of the mRNA. An overall increase in enzyme activity is moreover achieved by preventing degradation of the enzyme. These measures may optionally be combined at will.

The microorganisms, provided by the present invention, may produce L-amino acids, in particular L-glutamate, from glucose, sucrose, lactose, fructose, maltose, molasses, starch, cellulose or from glycerol and ethanol. The microorganisms may comprise representatives of the coryneform bacteria in particular of the genus Corynebacterium. Within the genus Corynebacterium, the species *Corynebacterium glutamicum* may in particular be mentioned, which is known in specialist circles for its ability to produce L-amino acids.

Suitable strains of the genus Corynebacterium, in particular of the species *Corynebacterium glutamicum*, are for example the known wild type strains

*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020

The present invention also provides an isolated polynucleotide from coryneform bacteria containing a polynucleotide sequence selected from the group a) polynucleotide which is at least 70% homologous to a polynucleotide which codes for a polypeptide containing the amino acid sequence of SEQ ID NO: 2, b) polynucleotide which codes for a polypeptide which contains an amino acid sequence which is at least 70% homologous to the amino acid sequence of SEQ ID NO: 2, c) polynucleotide which is complementary to the polynucleotides of a) or b), and d) polynucleotide containing at least 15 successive nucleotides of the polynucleotide sequence of a), b) or c).

For the purposes of the present application, a polynucleotide sequence is "homologous" to the sequence according to the invention if the base composition and sequence thereof at least 70%, preferably at least 80%, particularly preferably at least 90% matches the sequence according to the invention. According to the present invention, a "homologous protein" should be taken to mean proteins which have an amino acid sequence which at least 70%, preferably at least 80%, particularly preferably at least 90% matches the amino acid sequence which is coded by the cls gene (SEQ ID NO: 1), wherein "matching" should be taken to mean that the corresponding amino acids are either identical or comprise mutually homologous amino acids. "Homologous amino acids" are those having corresponding properties, in particular with regard to charge, hydrophobicity, steric properties etc.

The invention moreover provides a polynucleotide as described above, wherein it preferably comprises replicable DNA containing:

(i) the nucleotide sequence shown in SEQ ID NO: 1, or (ii) at least one sequence which corresponds to the sequence (i) within the degeneration range of the genetic code, or (iii) at least one sequence which hybridizes with the complementary sequence to sequence (i) or (ii) and optionally (iv) functionally neutral mutations in (i) which give rise to the same or a homologous amino acid.

The relative degree of substitution or mutation in the polynucleotide or amino acid sequence to produce a desired percentage of sequence identity can be established or determined by well-known methods of sequence analysis. These methods are disclosed and demonstrated in Bishop, et al. "DNA & Protein Sequence Analysis (A Practical Approach"), Oxford Univ. Press, Inc. (1997) *I.B.R.* and by Steinberg, Michael "Protein Structure Prediction" (A Practical Approach), Oxford Univ. Press, Inc. (1997) *I.B.R.* Hybridization of complementary sequences can occur at varying degrees of stringency. Sambrook et al.: Molecular Cloning, A Laboratory Manual (Cold Spring Harbor Laboratory Press, 1989) *I.B.R.*

Hybridization of complementary sequences can occur at varying degrees of stringency. Sambrook et al.: Molecular Cloning, A Laboratory Manual (Cold Spring Harbor Laboratory Press, 1989) *I.B.R.* Instructions for identifying DNA sequences by means of hybridization can be found by the expert, inter alia, in the handbook "The DIG System Users Guide for Filter Hybridization" from Boehringer Mannheim GmbH (Mannheim, Germany, 1993)*I.B.R.* and in Liebl et al. (International Journal of Systematic Bacteriology (1991) 41: 255–260)*I.B.R.*

Comprehensive descriptions can be found in known textbooks of genetics and molecular biology, such as e.g. that by Hagemann ("Allgemeine Genetik" [General Genetics], Gustav Fischer Verlag, Stuttgart, 1986) *I.B.R.*

Possible mutations are transitions, transversions, insertions and deletions. Depending on the effect of the amino acid exchange on the enzyme activity, missense mutations or nonsense mutations are referred to. Insertions or deletions of at least one base pair in a gene lead to frame shift mutations, as a consequence of which incorrect amino acids are incorporated or translation is interrupted prematurely. Deletions of several codons typically lead to a complete loss of the enzyme activity.

Instructions on generation of such mutations are prior art and can be found in known textbooks of genetics and molecular biology, such as e.g. the textbook by Knippers ("Molekulare Genetik" [Molecular Genetics], 6th edition, Georg Thieme Verlag, Stuttgart, Germany, 1995) *I.B.R.,* that by Winnacker ("Gene und Klone" [Genes and Clones], VCH Verlagsgesellschaft, Weinheim, Germany, 1990) *I.B.R.* or that by Hagemann ("Allgemeine Genetik" [General Genetics], Gustav Fischer Verlag, Stuttgart, 1986) *I.B.R.*

The invention also provides a vector containing one of the stated polynucleotides and coryneform bacteria acting as host cell which contain the vector or in which the cls gene is amplified.

The invention also provides a replicable polynucleotide which comprises or consists of the nucleotide sequence SEQ ID NO: 1, a polynucleotide which codes for a polypeptide which comprises or consists of the amino acid sequence SEQ ID NO: 2, a vector containing the DNA sequence of *C. glutamicum* which codes for the cls gene, contained in the vector (plasmid) pJC1cls, deposited in *Corynebacterium glutamicum* under the number DSM 13250, and coryneform bacteria acting as host cell which contain the vector or in which the cls gene is amplified.

The invention also provides polynucleotides which contain the complete gene with the polynucleotide sequence according to SEQ ID NO: 1 or fragments thereof and which are obtainable by screening by means of hybridization of a suitable gene library with a probe which contains the sequence of the stated polynucleotide according to SEQ ID NO: 1 or a fragment thereof and isolation of the stated DNA sequence.

Polynucleotide sequences according to the invention are also suitable as hybridization probes for RNA, cDNA and DNA in order to isolate full length cDNA which code for cardiolipin synthase and to isolate such cDNA or genes, which exhibit a high level of similarity with the sequence of the cardiolipin synthase gene.

Polynucleotide sequences according to the invention are furthermore suitable as primers for the polymerase chain reaction (PCR) for the production of DNA which codes for cardiolipin synthase.

Such oligonucleotides acting as probes or primers may contain more than 30, preferably up to 30, particularly preferably up to 20, very particularly preferably at least 15 successive nucleotides. Oligonucleotides having a length of at least 40 or 50 nucleotides are also suitable.

"Isolated" means separated from its natural environment.

"Polynucleotide" generally relates to polyribonucleotides and polydeoxyribonucleotides, wherein the RNA or DNA may be unmodified or modified.

"Polypeptides" are taken to mean peptides or proteins which contain two or more amino acids connected by peptide bonds.

The polypeptides according to the invention include a polypeptide according to SEQ ID NO: 2, in particular those having the biological activity of cardiolipin synthase and also those, which are at least 70%, preferably at least 80%, homologous to the polypeptide according to SEQ ID NO: 2 and in particular which exhibit 90% to 95% homology to the polypeptide according to SEQ ID NO: 2 and exhibit the stated activity.

The invention moreover relates to a process for the fermentative production of amino acids, in particular L-glutamate, using coryneform bacteria, which in particular already produce an amino acid and in which the nucleotide sequences which code for the cls gene are amplified, in particular overexpressed.

The present invention presents for the first time the cls gene of *C. glutamicum* which codes for cardiolipin synthase.

The cls gene or also other genes from *C. glutamicum* are isolated by initially constructing a gene library of this microorganism in *E. coli*. The construction of gene libraries is described in generally known textbooks and manuals. Examples which may be mentioned are the textbook by Winnacker, Gene und Klone, Eine Einführung in die Gentechnologie (Verlag Chemie, Weinheim, Germany, 1990) I.B.R. or the manual by Sambrook et al., Molecular Cloning, A Laboratory Manual (Cold Spring Harbor Laboratory Press, 1989) I.B.R. One very well known gene library is that of *E. coli* K-12 strain W3110, which was constructed by Kohara et al. (Cell 50, 495–508 (1987)) I.B.R. in λ-vectors. Bathe et al. (Molecular and General Genetics, 252:255–265, 1996) I.B.R. describe a gene library of *C. glutamicum* ATCC13032, which was constructed using the cosmid vector SuperCos I (Wahl et al., 1987, Proceedings of the National Academy of Sciences USA, 84:2160–2164) I.B.R. in *E. coli* K-12 strain NM554 (Raleigh et al., 1988, Nucleic Acids Research 16:1563–1575) I.B.R. Börmann et al. (Molecular Microbiology 6(3), 317–326, 1992)) I.B.R. also describe a gene library of *C. glutamicum* ATCC 13032, using cosmid pHC79 (Hohn and Collins, Gene 11, 291–298 (1980)). A gene library of *C. glutamicum* in *E. coli* may also be produced using plasmids such as pBR322 (Bolivar, Life Sciences, 25, 807–818 (1979)) I.B.R. or pUC9 (Vieira et al., 1982, Gene, 19:259–268) I.B.R. Suitable hosts are in particular those *E. coli* strains with restriction and recombination defects. One example of such a strain is the strain DH5αmcr, which has been described by Grant et al. (Proceedings of the National Academy of Sciences USA, 87 (1990) 4645–4649) I.B.R. The long DNA fragments cloned with the assistance of cosmids may then in turn be subcloned in usual vectors suitable for sequencing and then be sequenced, as described, for example, in Sanger et al. (Proceedings of the National Academy of Sciences of the United States of America, 74:5463–5467, 1977) I.B.R.

The novel DNA sequence from *C. glutamicum* which codes for the cls gene and, as SEQ ID NO: 1, is provided by the present invention, was obtained in this manner. The amino acid sequence of the corresponding protein was furthermore deduced from the above DNA sequence using the methods described above. SEQ ID NO: 2 shows the resultant amino acid sequence of the product of the cls gene.

Coding DNA sequences arising from SEQ ID NO: 1 due to the degeneracy of the genetic code are also provided by the invention. DNA sequences which hybridize with SEQ ID NO: 1 or parts of SEQ ID NO: 1 are similarly provided by the invention. Conservative substitutions of amino acids in proteins, for example the substitution of glycine for alanine or of aspartic acid for glutamic acid, are known in specialist circles as "sense mutations", which result in no fundamental change in activity of the protein, i.e. they are functionally neutral. It is furthermore known that changes to the N and/or C terminus of a protein do not substantially impair or may even stabilize the function thereof. The person skilled in the art will find information in this connection inter alia in Ben-Bassat et al. (Journal of Bacteriology 169:751–757 (1987)) I.B.R., in O'Regan et al. (Gene 77:237–251 (1989)) I.B.R., in Sahin-Toth et al. (Protein Sciences 3:240–247 (1994)) I.B.R., in Hochuli et al. (Bio/Technology 6:1321–1325 (1988)) I.B.R. and in known textbooks of genetics and molecular biology. Amino acid sequences arising in a corresponding manner from SEQ ID NO: 2 are also provided by the invention.

DNA sequences which hybridize with SEQ ID NO: 1 or parts of SEQ ID NO: 1 are similarly provided by the invention. Finally, DNA sequences produced by the polymerase chain reaction (PCR) using oligonucleotide primers obtained from SEQ ID NO: 1 are also provided by the invention. Such oligonucleotides typically have a length of at least 15 nucleotides.

The person skilled in the art may find instructions for identifying DNA sequences by means of hybridization inter alia in the manual "The DIG System Users Guide for Filter Hybridization" from Boehringer Mannheim GmbH (Mannheim, Germany, 1993) I.B.R. and in Liebl et al. (International Journal of Systematic Bacteriology (1991) 41: 255–260) I.B.R. The person skilled in the art may find instructions for amplifying DNA sequences using the polymerase chain reaction (PCR) inter alia in the manual by Gait, Oligonucleotide synthesis: a practical approach (IRL Press, Oxford, UK, 1984) I.B.R. and in Newton & Graham, PCR (Spektrum Akademischer Verlag, Heidelberg, Germany, 1994) I.B.R.

During work on the present invention, it proved possible to establish that coryneform bacteria produce amino acids, in particular L-glutamate, in an improved manner once the cls gene has been amplified.

The genes or gene constructs under consideration may either be present in plasmids in a variable copy number or be integrated into the chromosome and amplified. Alternatively, overexpression of the genes concerned may also be achieved by modifying the composition of the nutrient media and culture conditions.

The person skilled in the art will find guidance in this connection inter alia in Martin et al. (Bio/Technology 5, 137–146 (1987)) I.B.R., in Guerrero et al. (Gene 138, 35–41 (1994)) I.B.R., Tsuchiya and Morinaga (Bio/Technology 6, 428–430 (1988)) I.B.R., in Eikmanns et al. (Gene 102, 93–98 (1991)) I.B.R., in European patent EPS 0 472 869 I.B.R., in U.S. Pat. No. 4,601,893 I.B.R., in Schwarzer and Pühler (Bio/Technology 9, 84–87 (1991) I.B.R., in Reinscheid et al. (Applied and Environmental Microbiology 60, 126–132 (1994)) I.B.R., in LaBarre et al. (Journal of Bacteriology 175, 1001–1007 (1993)) I.B.R., in patent application WO 96/15246 I.B.R., in Malumbres et al. (Gene 134, 15–24 (1993)) I.B.R., in Japanese published patent application JP-A-10-229891 I.B.R., in Jensen and Hammer (Biotechnology and Bioengineering 58, 191–195 (1998)) I.B.R., in Makrides (Microbiological Reviews 60:512–538 (1996)) I.B.R. and in known textbooks of genetics and molecular biology.

By way of example, the cls gene according to the invention was overexpressed with the assistance of plasmids.

Suitable plasmids are those which are replicated and expressed in coryneform bacteria. Numerous known plasmid vectors, such as for example pZ1 (Menkel et al., Applied and Environmental Microbiology (1989) 64: 549–554) I.B.R., pEKEx1 (Eikmanns et al., Gene 102:93–98 (1991)) I.B.R. or pHS21 (Sonnen et al., Gene 107:69–74 (1991)) I.B.R. are based on the cryptic plasmids pHM1519, pBL1 or pGA1. Other plasmid vectors, such as for example those based on pCG4 (U.S. Pat. No. 4,489,160 I.B.R.), or pNG2 (Serwold-Davis et al., FEMS Microbiology Letters 66, 119–124 (1990) I.B.R.), or pAG1 (U.S. Pat. No. 5,158,891 I.B.R.) may be used in the same manner.

One example of a plasmid by means of which the cls gene may be overexpressed is pJC1cls (FIG. 1), which is based on the *E. coli-C. glutamicum* shuttle vector pJC1 (Cremer et al., 1990, Molecular and General Genetics 220: 478–480 I.B.R.) and contains the DNA sequence of *C. glutamicum* which codes for the cls gene. It is contained in the strain DSM5715/pJC1cls.

Further suitable plasmid vectors are those with the assistance of which gene amplification may be performed by integration into the chromosome, as has for example been described by Reinscheid et al. (Applied and Environmental Microbiology 60, 126–132 (1994) I.B.R.) for the duplication or amplification of the hom-thrB operon. In this method, the complete gene is cloned into a plasmid vector which can replicate in a host (typically *E. coli*), but not in *C. glutamicum*. Vectors which may be considered are, for example, pSUP301 (Simon et al., Bio/Technology 1, 784–791 (1983) I.B.R.), pK18mob or pK19mob (Schäfer et al., Gene 145, 69–73 (1994) I.B.R.), pGEM-T (Promega corporation, Madison, Wis., USA I.B.R.), pCR2.1-TOPO (Shuman (1994 I.B.R.). Journal of Biological Chemistry 269:32678–84 I.B.R.; U.S. Pat. No. 5,487,993 I.B.R.), pCR®Blunt (Invitrogen, Groningen, Netherlands; Bernard et al., Journal of Molecular Biology, 234: 534–541 (1993) I.B.R.) or pEM1 (Schrumpf et al, 1991, Journal of Bacteriology 173:4510–4516 I.B.R.). The plasmid vector which contains the gene to be amplified is then transferred into the desired strain of *C. glutamicum* by conjugation or transformation. The conjugation method is described, for example, in Schäfer et al. (Applied and Environmental Microbiology 60, 756–759 (1994) I.B.R.). Transformation methods are described, for example, in Thierbach et al. (Applied Microbiology and Biotechnology 29, 356–362 (1988) I.B.R.), Dunican and Shivnan (Bio/Technology 7, 1067–1070 (1989) I.B.R.) and Tauch et al. (FEMS Microbiological Letters 123, 343–347 (1994) I.B.R.). After homologous recombination by means of "crossing over", the resultant strain contains at least two copies of the gene in question.

It may additionally be advantageous for the production of amino acids, in particular L-glutamate, to amplify or overexpress not only the cls gene, but also one or more enzymes of the particular biosynthetic pathway, of glycolysis, of anaplerotic metabolism, of the citric acid cycle or of amino acid export.

For the production of L-glutamate, for example, it is thus possible simultaneously to amplify, in particular overexpress or amplify, one or more genes selected from the group the gdh gene which codes for glutamate dehydrogenase (DE: 19907347.3 I.B.R.) and/or the pyc gene which codes for pyruvate carboxylase (Peters-Wendisch et al. (1998), Microbiology 144: 915–927 I.B.R.).

It may furthermore be advantageous for the production of L-glutamate, in addition to amplifying the cls gene, simultaneously to attenuate the odhA gene which codes for α-ketoglutarate dehydrogenase (WO 9534672 A1 951221* I.B.R.), or the dtsR1 gene which codes for the DtsR1 protein (WO 952324 A1 950831* I.B.R.), or the dtsR2 gene which codes for the DtsR2 protein (WO 9902692A A1 990121* I.B.R.).

It may furthermore be advantageous for the production of amino acids, in particular L-glutamate, in addition to overexpressing the cls gene, to suppress unwanted secondary reactions (Nakayama: "Breeding of Amino Acid Producing Micro-organisms", in: Overproduction of Microbial Products, Krumphanzl, Sikyta, Vanek (eds.), Academic Press, London, UK, 1982) I.B.R.

For the purposes of amino acid production, in particular of L-glutamate, the microorganisms produced according to the invention may be cultured continuously or discontinuously using the batch process or the fed batch process or repeated fed batch process. A summary of known culture methods is given in the textbook by Chmiel (Bioprozeßtechnik 1. Einführung in die Bioverfahrenstechnik (Gustav Fischer Verlag, Stuttgart, 1991) I.B.R.) or in the textbook by Storhas (Bioreaktoren und periphere Einrichtungen (Vieweg Verlag, Braunschweig/Wiesbaden, 1994) I.B.R.).

The culture medium to be used must adequately satisfy the requirements of the particular strains. Culture media for various microorganisms are described in "Manual of Methods for General Bacteriology" from the American Society for Bacteriology (Washington D.C., USA, 1981) I.B.R. Carbon sources which may be used are sugars and carbohydrates, such as glucose, sucrose, lactose, fructose, maltose, molasses, starch and cellulose for example, oils and fats, such as soya oil, sunflower oil, peanut oil and coconut oil for example, fatty acids, such as palmitic acid, stearic acid and linoleic acid for example, alcohols, such as glycerol and ethanol for example, and organic acids, such as acetic acid for example. These substances may be used individually or as a mixture. Nitrogen sources which may be used comprise organic compounds containing nitrogen, such as peptones, yeast extract, meat extract, malt extract, corn steep liquor, soya flour and urea or inorganic compounds, such as ammonium sulfate, ammonium chloride, ammonium phosphate, ammonium carbonate and ammonium nitrate. The nitrogen sources may be used individually or as a mixture. Phosphorus sources which may be used are phosphoric acid, potassium dihydrogen phosphate or dipotassium hydrogen phosphate or the corresponding salts containing sodium. The culture medium must furthermore contain metal salts, such as for example magnesium sulfate or iron sulfate, which are necessary for growth. Finally, essential growth-promoting substances such as amino acids and vitamins may also be used in addition to the above stated substances. Suitable precursors may furthermore be added to the culture medium. The stated feed substances may be added to the culture as a single batch or be fed appropriately during culturing.

Basic compounds, such as sodium hydroxide, potassium hydroxide, ammonia or ammonia water, or acidic compounds, such as phosphoric acid or sulfuric acid, are used appropriately to control the pH of the culture. Foaming may be controlled by using antifoaming agents such as fatty acid polyglycol esters for example. Plasmid stability may be maintained by the addition to the medium of suitable selectively acting substances, for example antibiotics. Oxygen or oxygen-containing gas mixtures, such as air for example, are introduced into the culture in order to maintain aerobic conditions. The temperature of the culture is normally from 20° C. to 45° C. and preferably from 25° C. to 40° C. The culture is continued until the maximum quantity of glutamate has formed. This objective is normally achieved within 10 hours to 160 hours.

The following microorganism has been deposited with Deutsche Sammlung für Mikrorganismen und Zellkulturen (DSMZ, Braunschweig, Germany) in accordance with the Budapest Treaty:

*Corynebacterium glutamicum* strain DSM5715/pJC1cls as DSM13250

The purpose of the process according to the invention is the fermentative production of amino acids, in particular L-glutamate.

Key to the Figure:
FIG. 1: Map of the plasmid pJC1cls
The abbreviations and names are defined as follows:

| | |
|---|---|
| Orf2,rep: | plasmid-coded replication origin, C. glutamicum (from pHM1519) |
| lacZ-alpha`: | part of the 5' end of the β-galactosidase gene |
| cls: | cls (cardiolipin synthase) gene from C. glutamicum ATCC13032 |
| BamHI: | restriction site of the restriction enzyme BamHI |
| XbaI: | restriction site of the restriction enzyme XbaI |
| PstI: | restriction site of the restriction enzyme PstI |
| SalI: | restriction site of the restriction enzyme SalI |
| EcoRI: | restriction site of the restriction enzyme EcoRI |

EXAMPLES

The present invention is illustrated in greater detail by the following practical Examples.

Example 1

Production of a Genomic Cosmid Gene Library from *Corynebacterium glutamicum* ATCC13032

Chromosomal DNA from *Corynebacterium glutamicum* ATCC13032 was isolated as described in Tauch et al., (1995, Plasmid 33:168–179 I.B.R.) and partially cleaved with the restriction enzyme Sau3AI (Amersham Pharmacia, Freiburg, Germany, product description Sau3AI, code no. 27-0913-02 I.B.R.). The DNA fragments were dephosphorylated with shrimp alkaline phosphatase (Roche Molecular Biochemicals, Mannheim, Germany, product description SAP, code no. 1758250 I.B.R.). The DNA of cosmid vector SuperCos1 (Wahl et al. (1987) Proceedings of the National Academy of Sciences USA 84:2160–2164 I.B.R.), purchased from Stratagene (La Jolla, USA, product description SuperCos1 Cosmid Vector Kit, code no. 251301 I.B.R.) was cleaved with the restriction enzyme XbaI (Amersham Pharmacia, Freiburg, Germany, product description XbaI, Code no. 27-0948-02 I.B.R.) and also dephosphorylated with shrimp alkaline phosphatase. The cosmid DNA was then cleaved with the restriction enzyme BamHI (Amersham Pharmacia, Freiburg, Germany, product description BamHI, code no. 27-0868-04 I.B.R.). Cosmid DNA treated in this manner was mixed with the treated ATCC 13032 DNA and the batch was treated with T4 DNA ligase (Amersham Pharmacia, Freiburg, Germany, product description T4 DNA Ligase, code no. 27-0870-04 I.B.R.). The ligation mixture was then packed in phages using Gigapack II XL Packing Extracts (Stratagene, La Jolla, USA, product description Gigapack II XL Packing Extract, code no. 200217 I.B.R.). *E. coli* strain NM554 (Raleigh et al. 1988, Nucleic Acid Res. 16:1563–1575 I.B.R.) was infected by suspending the cells in 10 mM $MgSO_4$ and mixing them with an aliquot of the phage suspension. The cosmid library was infected and titred as described in Sambrook et al. (1989, Molecular Cloning: A laboratory Manual, Cold Spring Harbor I.B.R.), the cells being plated out on LB agar (Lennox, 1955, Virology, 1:190 I.B.R.) with 100 mg/l of ampicillin. After overnight incubation at 37° C., individual recombinant clones were selected.

Example 2

Isolation and Sequencing of the cls Gene

Cosmid DNA from an individual colony was isolated in accordance with the manufacturer's instructions using the Qiaprep Spin Miniprep Kit (Product No. 27106, Qiagen, Hilden, Germany) and partially cleaved with the restriction enzyme Sau3AI (Amersham Pharmacia, Freiburg, Germany, product description Sau3AI, product no. 27-0913-02). The DNA fragments were dephosphorylated with shrimp alkaline phosphatase (Roche Molecular Biochemicals, Mannheim, Germany, product description SAP, product no. 1758250). Once separated by gel electrophoresis, the cosmid fragments of a size of 1500 to 2000 bp were isolated using the QiaExII Gel Extraction Kit (product no. 20021, Qiagen, Hilden, Germany). The DNA of the sequencing vector pZero-1 purchased from Invitrogen (Groningen, Netherlands, product description Zero Background Cloning Kit, product no. K2500-01) was cleaved with the restriction enzyme BamHI (Amersham Pharmacia, Freiburg, Germany, product description BamHI, Product No. 27-0868-04). Ligation of the cosmid fragments into the sequencing vector pZero-1 was performed as described by Sambrook et al. (1989, Molecular Cloning: A laboratory Manual, Cold Spring Harbor I.B.R.), the DNA mixture being incubated overnight with T4 ligase (Pharmacia Biotech, Freiburg, Germany). This ligation mixture was then electroporated into the *E. coli* strain DH5αMCR (Grant, 1990, Proceedings of the National Academy of Sciences U.S.A., 87:4645–4649 I.B.R.) (Tauch et al. 1994, FEMS Microbiol Letters, 123:343–7 I.B.R.) and plated out onto LB agar (Lennox, 1955, Virology, 1:190 I.B.R.) with 50 mg/l of Zeocin. Plasmids of the recombinant clones were prepared using the Biorobot 9600 (product no. 900200, Qiagen, Hilden, Germany). Sequencing was performed using the dideoxy chain termination method according to Sanger et al. (1977, Proceedings of the National Academy of Sciences U.S.A., 74:5463–5467 I.B.R.) as modified by Zimmermann et al. (1990, Nucleic Acids Research, 18:1067 I.B.R.). The "RR dRhodamin Terminator Cycle Sequencing Kit" from PE Applied Biosystems (product no. 403044, Weiterstadt, Germany) was used. Separation by gel electrophoresis and analysis of the sequencing reaction was performed in a "Rotiphorese NF" acrylamide/bisacrylamide gel (29:1) (product no. A124.1, Roth, Karlsruhe, Germany) using the "ABI Prism 377" sequencer from PE Applied Biosystems (Weiterstadt, Germany).

The resultant raw sequence data were then processed using the Staden software package (1986, Nucleic Acids Research, 14:217–231 I.B.R.), version 97-0. The individual sequences of the pZero 1 derivatives were assembled into a cohesive contig. Computer-aided coding range analysis was performed using XNIP software (Staden, 1986, Nucleic Acids Research, 14:217–231 I.B.R.). Further analysis was performed using the "BLAST search programs" (Altschul et al., 1997, Nucleic Acids Research, 25:3389–3402 I.B.R.), against the non-redundant database of the "National Center for Biotechnology Information" (NCBI, Bethesda, Md., USA I.B.R.).

The resultant nucleotide sequence is stated in SEQ ID NO: 1. Analysis of the nucleotide sequence revealed an open reading frame of 1502 base pairs, which was designated the cls gene. The cls gene codes for a protein of 500 amino acids (SEQ ID NO: 2).

Example 3

Cloning of the cls Gene Into Vector pJC1

Chromosomal DNA from *Corynebacterium glutamicum* ATCC 13032 was isolated as described in Tauch et al., (1995, Plasmid 33:168–179 I.B.R.). A DNA fragment bearing the cis gene was amplified with the assistance of the polymerase chain reaction. The following primers were used for this purpose:

(SEQ ID NO: 3)
5'-TGC TCT AGA CGG TAA GTC GGT CCC TCT AAA AG-3'

(SEQ ID NO: 4)
5'-TGC TCT AGA CAA CCG GCG CCT CTG ACC AC-3'

Both oligonucleotides bear the sequence for the cleavage site of the restriction enzyme XbaI (underlined nucleotides). The stated primers were synthesized by the company MWG Biotech (Ebersberg, Germany) and the PCR reaction was performed in accordance with the standard PCR method of Innis et al. (PCR protocol. A guide to methods and applications, 1990, Academic Press I.B.R.). The primers allow the 1610 bp DNA fragment which bears the cls gene from *Corynebacterium glutamicum* to be amplified.

Once separated by gel electrophoresis, the PCR fragment was isolated from the agarose gel using the QiaExII Gel Extraction Kit (product no. 20021, Qiagen, Hilden, Germany).

The PCR fragment obtained in this manner was completely cleaved with the restriction enzyme XbaI. The approx. 1600 bp cls fragment was isolated from the agarose gel using the QiaExII Gel Extraction Kit (product no. 20021, Qiagen, Hilden, Germany).

The vector used was the *E. coli-C. glutamicum* shuttle vector pJC1 (Cremer et al., 1990, Molecular and General Genetics 220: 478–480 I.B.R.). This plasmid was also completely cleaved with the restriction enzyme XbaI and then dephosphorylated with shrimp alkaline phosphatase (Roche Diagnostics GmbH, Mannheim, Germany, product description SAP, product no. 1758250).

The cls fragment obtained in this manner was mixed with the prepared pJC1 vector and the batch was treated with T4 DNA ligase (Amersham Pharmacia, Freiburg, Germany, product description T4 DNA Ligase, code no. 27-0870-04). The ligation batch was then transformed into *E. coli* strain DH5α (Hanahan, in: DNA cloning. A practical approach. Vol. I. IRL-Press, Oxford, Washington D.C., USA). Plasmid-bearing cells were selected by plating the transformation batch out onto LB agar (Lennox, 1955, Virology, 1:190 I.B.R.) with 50 mg/l of kanamycin. After overnight incubation at 37° C., individual recombinant clones were selected. Plasmid DNA was isolated from a transformant in accordance with the manufacturer's instructions using the Qiaprep Spin Miniprep Kit (product no. 27106, Qiagen, Hilden, Germany) and cleaved with the restriction enzyme XbaI in order to check the plasmid by subsequent agarose gel electrophoresis. The resultant plasmid was named pJC1cls.

Example 4

Transformation of Strain ATCC13032 with Plasmid pJC1cls

Strain ATCC 13032 was then transformed with plasmid pJC1cls using the electroporation method described by Liebl et al. (FEMS Microbiology Letters, 53:299–303 (1989) I.B.R.) Transformant selection proceeded on LBHIS agar consisting of 18.5 g/l of brain-heart infusion bouillon, 0.5 M sorbitol, 5 g/l of Bacto tryptone, 2.5 g/l of Bacto yeast extract, 5 g/l of NaCl and 18 g/l of Bacto agar, which had been supplemented with 25 mg/l of kanamycin. Incubation was performed for 2 days at 33° C.

Plasmid DNA was isolated from a transformant using the conventional methods (Peters-Wendisch et al., 1998, Microbiology, 144, 915–927 I.B.R.), cut with the restriction endonuclease XbaI and the plasmid to be checked by subsequent agarose gel electrophoresis. The resultant strain was named ATCC13032/pJC1cls.

The following microorganism has been deposited with Deutsche Sammlung für Mikrorganismen und Zellkulturen (DSMZ, Braunschweig, Germany) in accordance with the Budapest Treaty:

*Corynebacterium glutamicum* strain DSM 5715/pJC1cls as DSM 13250

Example 5

Production of Glutamate

The *C. glutamicum* strain ATCC13032/pJC1cls obtained in Example 5 was cultured in a nutrient medium suitable for the production of glutamate and the glutamate content of the culture supernatant was determined.

To this end, the strain was initially incubated for 24 hours at 33° C. on an agar plate with the appropriate antibiotic (brain/heart agar with kanamycin (50 mg/l)). Starting from this agar plate culture, a preculture was inoculated (10 ml of medium in a 100 ml Erlenmeyer flask). The medium used for the preculture was complete medium CgIII (2.5 g/l of NaCl, 10 g/l of Bacto peptone, 10 g/l of Bacto yeast extract, 20 g/l of glucose, pH 7.4). Kanamycin (25 mg/l) was added to this medium. The preculture was incubated for 16 hours at 33° C. on a shaker at 240 rpm. A main culture was inoculated from this preculture, such that the initial OD (660 nm) of the main culture was 0.1.

After preculturing in medium CgIII (Keilhauer et al. 1993, Journal of Bacteriology 175:5595–5603 I.B.R.), strain ATCC13032/pJC1cls was cultured for the main culture in production medium CgXII (Keilhauer et al. 1993, Journal of Bacteriology 175:5595–5603 I.B.R.). 4% of glucose and 50 mg/l of kanamycin sulfate were added.

Culturing is performed in a volume of 10 ml in a 100 ml Erlenmeyer flask with flow spoilers. Kanamycin (25 mg/l) was added. Culturing was performed at 33° C. and 80% atmospheric humidity.

In order to induce glutamate formation, 20 g of Tween 60 (P-1629 Sigma-Aldrich, Deisenhofen, Germany) plus 80 ml of water were mixed and autoclaved. Some 4 hours after inoculation, 75 µl of this Tween solution were added to the culture and culturing was continued.

After 48 hours, the OD was determined at a measurement wavelength of 660 nm using a Biomek 1000 (Beckmann Instruments GmbH, Munich). The quantity of glutamate formed was determined using an amino acid analyzer from Eppendorf-BioTronik (Hamburg, Germany) by ion exchange chromatography and post-column derivatization with ninhydrin detection.

Table 1 shows the result of the test.

TABLE 1

| Strain | OD (660) | Glutamate-HCl mM |
|---|---|---|
| ATCC13032/pJC1cls | 13.9 | 102 |
| ATCC13032 | 13.8 | 94 |

We claim:

1. A genetically modified coryneform bacterium, wherein the cls gene thereof, which codes for cardiolipin synthase, is amplified.

2. The genetically modified coryneform bacterium as claimed in claim 1, wherein the starting bacterium (wild type) is selected from the group consisting of *Corynebacterium glutamicum* (ATCC13032), *Corynebacterium acetoglutamicum* (ATCC15806), *Corynebacterium acetoacidophilum* (ATCC13870), *Corynebacterium thermoaminogenes* (FERM BP-1539), *Corynebacterium melassecola* (ATCC17965), *Brevibacterium flavum* (ATCC14067), *Brevibacterium lactofermentum* (ATCC13869) and *Brevibacterium divaricatum* (ATCC14020).

3. The genetically modified coryneform bacterium as claimed in claim 1, wherein the cls gene is amplified by overexpressing the gene.

4. The genetically modified coryneform bacterium as claimed in claim 1, wherein the strain is transformed with a plasmid vector and the plasmid vector bears the nucleotide sequence which codes for the cls gene.

5. An isolated polynucleotide which encodes a protein comprising the amino acid sequence of SEQ ID NO: 2, wherein said protein has cardiolipin synthase activity.

6. The isolated polynucleotide according to claim 5, wherein said polynucleotide is isolated from a coryneform bacterium.

7. An isolated polynucleotide comprising nucleotides 154 to 1653 of SEQ ID NO: 1 or degenerate variants thereof.

8. An isolated polynucleotide comprising SEQ ID NO: 1.

9. An isolated polynucleotide consisting of SEQ ID NO: 1 or fragments thereof which encode a protein consisting of the amino acid sequence of SEQ ID NO: 2.

10. An isolated polynucleotide comprising the complement of SEQ ID NO: 1.

11. An isolated polynucleotide comprising a nucleotide sequence that is least 70% identical to the polynucleotide of SEQ ID NO: 1, wherein said polynucleotide encodes a protein comprising the amino acid sequence of SEQ ID NO: 2, and wherein said protein has cardiolipin synthase activity.

12. The isolated polynucleotide according to claim 11, wherein said nucleotide sequence is at least 80% identical to the polynucleotide of SEQ ID NO: 1.

13. The isolated polynucleotide according to claim 11, wherein said nucleotide sequence is at least 90% identical to the polynucleotide of SEQ ID NO: 1.

14. The isolated polynucleotide according to claim 11, wherein said polynucleotide is isolated from a Coryneform bacterium.

15. The isolated polynucleotide according to claim 12, wherein said polynucleotide is isolated from a Coryneform bacterium.

16. The isolated polynucleotide according to claim 13, wherein said polynucleotide is isolated from a Coryneform bacterium.

17. An isolated polynucleotide consisting of at least 15 consecutive nucleotides selected from one of SEQ ID NO: 1 or a complement of SEQ ID NO: 1.

18. The isolated polynucleotide of claim 17, wherein the polynucleotide is a probe that detects a polynucleotide that encodes a cls polypeptide consisting of SEQ ID NO: 2.

19. The isolated polynucleotide of claim 17, wherein the polynucleotide is a primer for use in a polymerase chain reaction for synthesizing a polynucleotide encoding a cls polypeptide consisting of SEQ ID NO: 2.

20. A vector comprising the isolated polynucleotide sequence of any one of claims 5 to 16.

21. A bacterium comprising the vector of claim 20.

22. A pJC1 cls vector contained in a coryneform bacterium deposited under DSM13250.

23. A bacterium comprising the vector of claim 22.

24. A coryneform bacterium comprising an isolated polynucleotide which encodes a protein comprising the amino acid sequence of SEQ ID NO: 2, wherein said protein has cardiolipin synthase activity.

25. The bacterium of claim 24, wherein said polynucleotide is amplified.

26. The bacterium of claim 25, wherein said polynucleotide is amplified by overexpression.

27. The bacterium of claim 24, wherein said bacterium is selected from the group consisting of *Corynebacterium glutamicum* (ATCC 13032), *Corynebacterium acetoglutamicum* (ATCC 15806), *Corynebacterium acetoacidophilum* (ATCC 13870), *Corynebacterium thermoaminogenes* (FERM BP-1539), *Corynebacterium melassecola* (ATCC 17965), *Brevibacterium flavum* (ATCC 14067), *Brevibacterium lactofermentum* (ATCC13869) and *Brevibacterium divaricatum* (ATCC14020).

28. The bacterium of claim 25, wherein said bacterium is selected from the group consisting of Corynebacterium glutamicum (ATCC 13032), *Corynebacterium acetoglutamicum* (ATCC 15806), *Corynebacterium acetoacidophilum* (ATCC 13870), *Corynebacterium thermoaminogenes* (FERM BP-1539), *Corynebacterium melassecola* (ATCC 17965), *Brevibacterium flavum* (ATCC 14067), *Brevibacterium lactofermentum* (ATCC 13869) and *Brevibacterium divaricatum* (ATCC 14020).

29. A *Corynebacterium glutamicum* DSM5715/pJC1 cls deposited under DSM 13250.

* * * * *

SEQUENCE LISTING

<160> NUMBER OF SEQ ID NOS: 4

<210> SEQ ID NO 1
<211> LENGTH: 1850
<212> TYPE: DNA
<213> ORGANISM: Corynebacterium glutamicum
<220> FEATURE:
<221> NAME/KEY: CDS
<222> LOCATION: (154)..(1653)
<223> OTHER INFORMATION:
<220> FEATURE:
<221> NAME/KEY: RBS
<222> LOCATION: (138)..(146)
<223> OTHER INFORMATION:

<400> SEQUENCE: 1

```
ctcaaaggcg aaggcatgcg catcgatttc cagctcgcat ccccggccct tgctgcaacc      60
gcgggtgaaa cctttgtgga cgttgaagaa cgcagcggaa ccggcgcctc tgaccacgca     120
ccagtcatcg ttgattacaa ggtgtaactg cgt atg atc ttt cag atc aac ctc     174
                                    Met Ile Phe Gln Ile Asn Leu
                                    1               5 gaa tct tgg caa acc gtt ggt ttg atc atc gac tac acc atc aaa atc      222
Glu Ser Trp Gln Thr Val Gly Leu Ile Ile Asp Tyr Thr Ile Lys Ile
        10                  15                  20 atc gcc att ggc tac gta ccc gaa gga cgc cga ccc agc tcc tcc acc      270
Ile Ala Ile Gly Tyr Val Pro Glu Gly Arg Arg Pro Ser Ser Ser Thr
25                  30                  35 gcg tgg ctc ctg gca att ttg ctg ctc ccc tac gtc gga ctc cca ctg      318
Ala Trp Leu Leu Ala Ile Leu Leu Leu Pro Tyr Val Gly Leu Pro Leu
40                  45                  50                  55 ttc ctg ctt atg gga tcg cca tac atc aac cgg cga cgc cac cgc atc      366
Phe Leu Leu Met Gly Ser Pro Tyr Ile Asn Arg Arg Arg His Arg Ile
                60                  65                  70 caa caa gaa atc aac gac ctc atc gaa gac gtc cac gac gac gtc ccc      414
Gln Gln Glu Ile Asn Asp Leu Ile Glu Asp Val His Asp Asp Val Pro
            75                  80                  85 gac atc ccc acc gga atg gat gtc tcc gcg gaa gtt gaa tct gtc atc      462
Asp Ile Pro Thr Gly Met Asp Val Ser Ala Glu Val Glu Ser Val Ile
        90                  95                 100 aaa ctc aac cgc cgc ctc acc cgc atg cca gca gtg acc ggc gga aac      510
Lys Leu Asn Arg Arg Leu Thr Arg Met Pro Ala Val Thr Gly Gly Asn
105                 110                 115 aac ggc ttc tac tcc gac tac cgt gaa tcc ctc aaa cgg atg acc gcc      558
Asn Gly Phe Tyr Ser Asp Tyr Arg Glu Ser Leu Lys Arg Met Thr Ala
120                 125                 130                 135 gca atc gac gaa gcc gaa gaa tac atc tac gtc gag atc tac atc atg      606
Ala Ile Asp Glu Ala Glu Glu Tyr Ile Tyr Val Glu Ile Tyr Ile Met
                140                 145                 150 gcc tgg gat tcc tac acc caa cca ttc ttc gca gca ctc gaa cga gcc      654
Ala Trp Asp Ser Tyr Thr Gln Pro Phe Phe Ala Ala Leu Glu Arg Ala
            155                 160                 165 cac aac cgc ggc gtc aaa gtc cga ctc ctt ttc gac cac gtc ggc agc      702
His Asn Arg Gly Val Lys Val Arg Leu Leu Phe Asp His Val Gly Ser
        170                 175                 180 tgg aaa tac ccc ggc tac cac cgc ctc aaa aaa gaa ctc aac cgc atg      750
Trp Lys Tyr Pro Gly Tyr His Arg Leu Lys Lys Glu Leu Asn Arg Met
185                 190                 195 ggc ttc gcc tgg tac ctc atg ctc ccc ctc caa ccc tgg cga cgc cgc      798
Gly Phe Ala Trp Tyr Leu Met Leu Pro Leu Gln Pro Trp Arg Arg Arg
200                 205                 210                 215
```

-continued

```
ttc cgc cga ccc gac ctg cgc aac cac cgc aaa atg ctc atc atc gac      846
Phe Arg Arg Pro Asp Leu Arg Asn His Arg Lys Met Leu Ile Ile Asp
            220                 225                 230 ggc cac acc gca ttc atg ggc tcc caa aat ctc atc gcc ccg agt tac      894
Gly His Thr Ala Phe Met Gly Ser Gln Asn Leu Ile Ala Pro Ser Tyr
            235                 240                 245 cta caa aag aaa aac atc aaa ctc ggc cgc gaa tgg aaa gac ctc atg      942
Leu Gln Lys Lys Asn Ile Lys Leu Gly Arg Glu Trp Lys Asp Leu Met
        250                 255                 260 gtc gaa ctc acc ggc ccc atc gtc tcc tcc atg gaa atg atc ttc gcc      990
Val Glu Leu Thr Gly Pro Ile Val Ser Ser Met Glu Met Ile Phe Ala
265                 270                 275 ggc gac tgg tac gtc gaa tcc aac gaa gcc ctc gac atc cgc gac cac     1038
Gly Asp Trp Tyr Val Glu Ser Asn Glu Ala Leu Asp Ile Arg Asp His
280                 285                 290                 295 gca gaa gcc cac ggc tac atc ggc aac act caa aaa gac tcc gcc acc     1086
Ala Glu Ala His Gly Tyr Ile Gly Asn Thr Gln Lys Asp Ser Ala Thr
                300                 305                 310 aac ctc gtg cag ctc atc ccc tcc ggc cct ggt tac acc aca gaa ccc     1134
Asn Leu Val Gln Leu Ile Pro Ser Gly Pro Gly Tyr Thr Thr Glu Pro
            315                 320                 325 aac ctg cgc atg ttc aac tcc atc gtt cac cac gcc aaa gaa cga ctc     1182
Asn Leu Arg Met Phe Asn Ser Ile Val His His Ala Lys Glu Arg Leu
            330                 335                 340 atc ttg tgc agc ccc tac ttc atc ccc gac gaa tcc ctc ctc gaa gcc     1230
Ile Leu Cys Ser Pro Tyr Phe Ile Pro Asp Glu Ser Leu Leu Glu Ala
        345                 350                 355 gtc acc tca gcc tgc tac cgc gga gta acc gtc gaa cta ttc gtc tct     1278
Val Thr Ser Ala Cys Tyr Arg Gly Val Thr Val Glu Leu Phe Val Ser
360                 365                 370                 375 gaa caa gcc gac caa ttc gcc atc gac cac gcc caa tcc tcc tac tac     1326
Glu Gln Ala Asp Gln Phe Ala Ile Asp His Ala Gln Ser Ser Tyr Tyr
                380                 385                 390 cag gca ctc ctt gaa gcc ggc gtg aaa atc tac caa ttc ccc aaa ccc     1374
Gln Ala Leu Leu Glu Ala Gly Val Lys Ile Tyr Gln Phe Pro Lys Pro
            395                 400                 405 gac gtc ctc cac acc aag tac atg atc gcc gac ccc gac gac acc acc     1422
Asp Val Leu His Thr Lys Tyr Met Ile Ala Asp Pro Asp Asp Thr Thr
            410                 415                 420 ggc aac gaa gcc ctc gga gtc ctc gga tcc tcc aac ctc gac atc cgc     1470
Gly Asn Glu Ala Leu Gly Val Leu Gly Ser Ser Asn Leu Asp Ile Arg
        425                 430                 435 agc ttt ggc ctc aac tac gaa atc tcc ctg atg atc gcc aaa ggc aac     1518
Ser Phe Gly Leu Asn Tyr Glu Ile Ser Leu Met Ile Ala Lys Gly Asn
440                 445                 450                 455 ctc atc cac gaa ctc aac gcc ctc acc gac cgt tac cgc aca gta agt     1566
Leu Ile His Glu Leu Asn Ala Leu Thr Asp Arg Tyr Arg Thr Val Ser
                460                 465                 470 ttc aag ctc acc ttg gat aag tgg aac cag cgc agt tgg cgg cgc cgc     1614
Phe Lys Leu Thr Leu Asp Lys Trp Asn Gln Arg Ser Trp Arg Arg Arg
            475                 480                 485 tac gtg gac aat gtc atg cgt ttg acc tcg gcg ctg cag tagtttggcg      1663
Tyr Val Asp Asn Val Met Arg Leu Thr Ser Ala Leu Gln
            490                 495                 500 cgtttggagt gcgtttgagg tggcttttag agggaccgac ttacccatcg ccattatgca   1723
aatatccgtt cgaaactttg gtcgggccac gcgtttgtgg tggattttg cacccttgcag   1783 ccagtttgat gcgaaaattc gttcggttta atggtcgggc cacgcgtttg tggtggaaat   1843
```

-continued ttgatca                                                                1850

<210> SEQ ID NO 2
<211> LENGTH: 500
<212> TYPE: PRT
<213> ORGANISM: Corynebacterium glutamicum

<400> SEQUENCE: 2

```
Met Ile Phe Gln Ile Asn Leu Glu Ser Trp Gln Thr Val Gly Leu Ile
1               5                   10                  15

Ile Asp Tyr Thr Ile Lys Ile Ala Ile Gly Tyr Val Pro Glu Gly
            20                  25                  30

Arg Arg Pro Ser Ser Thr Ala Trp Leu Leu Ala Ile Leu Leu Leu
        35                  40                  45

Pro Tyr Val Gly Leu Pro Leu Phe Leu Leu Met Gly Ser Pro Tyr Ile
50                  55                  60

Asn Arg Arg Arg His Arg Ile Gln Gln Glu Ile Asn Asp Leu Ile Glu
65                  70                  75                  80

Asp Val His Asp Val Pro Asp Ile Pro Thr Gly Met Asp Val Ser
            85                  90                  95

Ala Glu Val Glu Ser Val Ile Lys Leu Asn Arg Arg Leu Thr Arg Met
            100                 105                 110

Pro Ala Val Thr Gly Gly Asn Asn Gly Phe Tyr Ser Asp Tyr Arg Glu
            115                 120                 125

Ser Leu Lys Arg Met Thr Ala Ala Ile Asp Glu Ala Glu Glu Tyr Ile
        130                 135                 140

Tyr Val Glu Ile Tyr Ile Met Ala Trp Asp Ser Tyr Thr Gln Pro Phe
145                 150                 155                 160

Phe Ala Ala Leu Glu Arg Ala His Asn Arg Gly Val Lys Val Arg Leu
                165                 170                 175

Leu Phe Asp His Val Gly Ser Trp Lys Tyr Pro Gly Tyr His Arg Leu
            180                 185                 190

Lys Lys Glu Leu Asn Arg Met Gly Phe Ala Trp Tyr Leu Met Leu Pro
        195                 200                 205

Leu Gln Pro Trp Arg Arg Arg Phe Arg Arg Pro Asp Leu Arg Asn His
    210                 215                 220

Arg Lys Met Leu Ile Ile Asp Gly His Thr Ala Phe Met Gly Ser Gln
225                 230                 235                 240

Asn Leu Ile Ala Pro Ser Tyr Leu Gln Lys Lys Asn Ile Lys Leu Gly
                245                 250                 255

Arg Glu Trp Lys Asp Leu Met Val Glu Leu Thr Gly Pro Ile Val Ser
            260                 265                 270

Ser Met Glu Met Ile Phe Ala Gly Asp Trp Tyr Val Glu Ser Asn Glu
        275                 280                 285

Ala Leu Asp Ile Arg Asp His Ala Glu Ala His Gly Tyr Ile Gly Asn
    290                 295                 300

Thr Gln Lys Asp Ser Ala Thr Asn Leu Val Gln Leu Ile Pro Ser Gly
305                 310                 315                 320

Pro Gly Tyr Thr Thr Glu Pro Asn Leu Arg Met Phe Asn Ser Ile Val
                325                 330                 335

His His Ala Lys Glu Arg Leu Ile Leu Cys Ser Pro Tyr Phe Ile Pro
            340                 345                 350

Asp Glu Ser Leu Leu Glu Ala Val Thr Ser Ala Cys Tyr Arg Gly Val
        355                 360                 365
```

-continued

```
Thr Val Glu Leu Phe Val Ser Glu Gln Ala Asp Gln Phe Ala Ile Asp
    370             375             380

His Ala Gln Ser Ser Tyr Tyr Gln Ala Leu Leu Glu Ala Gly Val Lys
385             390             395                 400

Ile Tyr Gln Phe Pro Lys Pro Asp Val Leu His Thr Lys Tyr Met Ile
            405             410             415

Ala Asp Pro Asp Asp Thr Thr Gly Asn Glu Ala Leu Gly Val Leu Gly
            420             425             430

Ser Ser Asn Leu Asp Ile Arg Ser Phe Gly Leu Asn Tyr Glu Ile Ser
        435             440             445

Leu Met Ile Ala Lys Gly Asn Leu Ile His Glu Leu Asn Ala Leu Thr
    450             455             460

Asp Arg Tyr Arg Thr Val Ser Phe Lys Leu Thr Leu Asp Lys Trp Asn
465             470             475                 480

Gln Arg Ser Trp Arg Arg Arg Tyr Val Asp Asn Val Met Arg Leu Thr
            485             490             495

Ser Ala Leu Gln
            500
```

<210> SEQ ID NO 3
<211> LENGTH: 32
<212> TYPE: DNA
<213> ORGANISM: Corynebacterium glutamicum

<400> SEQUENCE: 3
tgctctagac ggtaagtcgg tccctctaaa ag         32

<210> SEQ ID NO 4
<211> LENGTH: 29
<212> TYPE: DNA
<213> ORGANISM: Corynebacterium glutamicum

<400> SEQUENCE: 4
tgctctagac aaccggcgcc tctgaccac           29